United States Patent [19]
Reichert

[11] Patent Number: 5,301,543
[45] Date of Patent: Apr. 12, 1994

[54] MOISTURE MONITOR IN A NON-CONDUCTIVE LIQUID MEDIA

[75] Inventor: Ralph Reichert, Belmont, Calif.

[73] Assignee: Adfiltech Corporation, Alexandria, Va.

[21] Appl. No.: 985,816

[22] Filed: Dec. 4, 1992

[51] Int. Cl.$^5$ .................................. G01N 27/02
[52] U.S. Cl. .................. 73/64.45; 73/64.44; 436/40
[58] Field of Search ............... 73/29.01, 53.01, 64.45, 73/64.46, 64.44, 29.02, 29.03; 436/39, 40

[56] References Cited

U.S. PATENT DOCUMENTS

| | | | |
|---|---|---|---|
| 3,077,105 | 2/1963 | Ohlheiser | 73/64.45 |
| 3,133,437 | 5/1964 | Remke et al. | 73/61.44 |
| 3,857,284 | 12/1974 | Carron et al. | 73/29.01 |
| 3,937,063 | 2/1976 | Kethley | 73/29.02 |
| 4,269,060 | 5/1981 | Keethley | 73/29.02 |
| 4,395,903 | 8/1983 | Gouw | 73/64.45 |

*Primary Examiner*—Robert J. Warden
*Assistant Examiner*—T. A. Trembley
*Attorney, Agent, or Firm*—Fisher & Associates

[57] ABSTRACT

A moisture monitor for determining the amount of moisture in liquids which may include direct installation into a non-conductive liquid flow line or, a detection chamber having a continuous flow of contaminated non-conductive liquid therethrough, and a probe inserted in the detection chamber including means for determining both actual water vapor pressure and saturation vapor pressure of water at the temperature of the liquid. An analyzer monitor remote from the probe is connected thereto by cable for converting the information received by the probe into an analysis of the moisture content of the liquid. Analyzer may be a separate control box or incorporated into remote equipment panel.

8 Claims, 1 Drawing Sheet

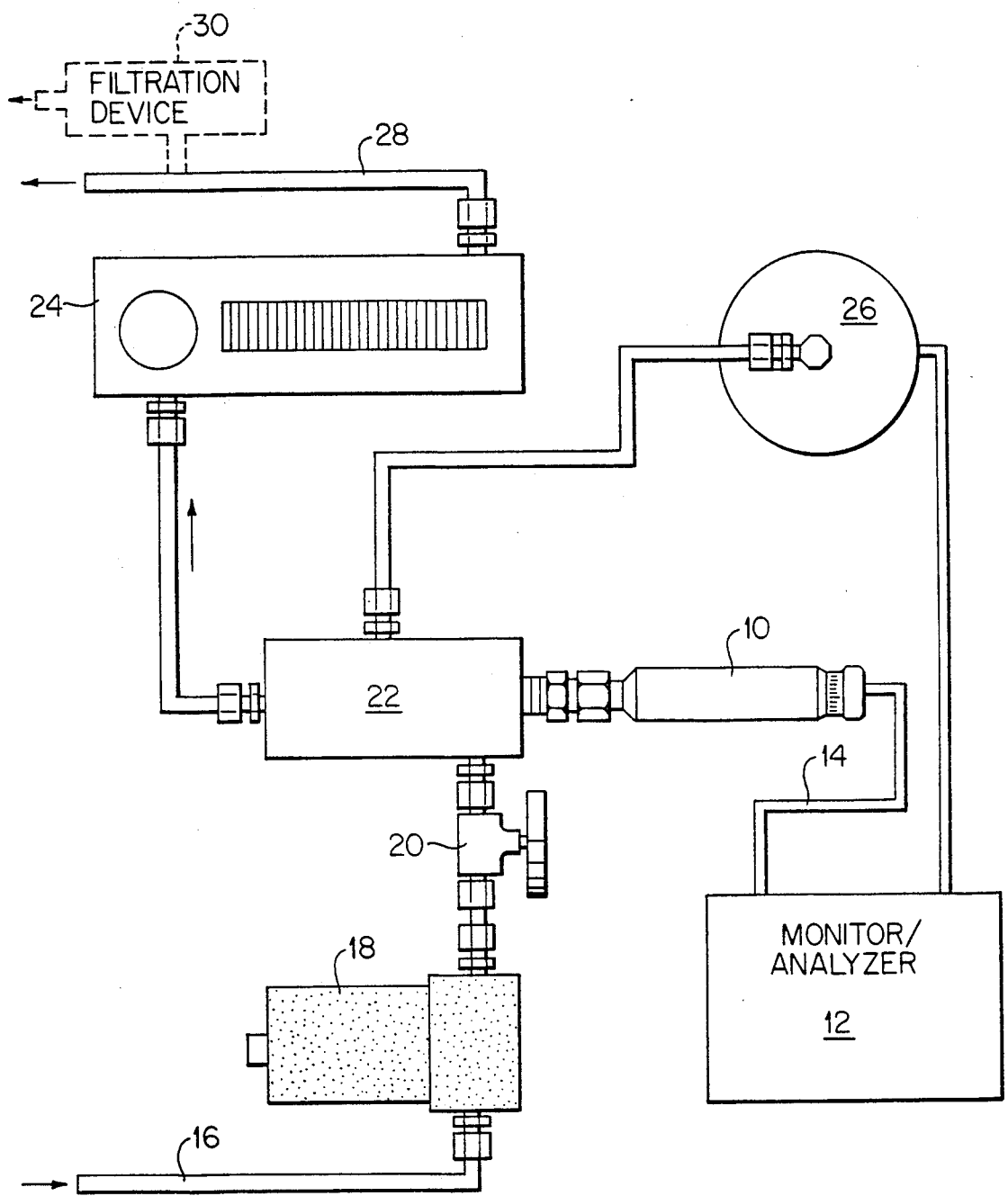

MOISTURE MONITOR IN A NON-CONDUCTIVE LIQUID MEDIA

BACKGROUND OF THE INVENTION

1. Field of the Invention

The present invention relates generally to a monitor for determining the amount of moisture in fluids, and more particularly to a monitor for determining the amount of moisture in liquids as express in parts per million by weight PPM$_w$.

2. Description of the Prior Art

Liquids consisting of nonpolar molecules such as hydrocarbon chains in oils or hydrocarbon rings in benzene, toluene, etc. do not mix with water. Similar to gases, liquid hydrocarbons can absorb a certain amount of water vapor and thus have a moisture concentration or saturation value. In contrast to gasses, liquids have individual saturation values. These values are temperature dependent and raise with increasing temperature. The similarity of non polar liquids to gasses allows moisture measurement with the gold/aluminum oxide sensor since the measurement is only influenced by the water molecules.

Numerous analytical techniques have been suggested for the determination of moisture in liquids. The majority of the commonly used methods are batch techniques, and require sample collection and transfer prior to laboratory analysis. The most generally used procedures employ the "Karl Fischer" reagent. This has become the accepted method of water determination. Although the "Karl Fisher" method has wide acceptance, several limitations have indicated the need for more reliable methods. There is a necessity to withdraw a sample from a fluid line, in a separate container which is free from adverse atmospheric conditions. Transferring this container to the laboratory and finally transferring the sample to another container creates exposure to strong oxidizing or reducing agents. The detection of the Karl Fischer end point requires careful technique and experience if the method is to provide reliable analyses.

The standard ASTM test for water, D1533, which involves the use of jars, has the disadvantage that the oil sample comes in contact with the atmosphere both at the time of sampling and at the time of analysis. Since moisture is present in atmospheric air, there is always the chance that the sample will become contaminated and an inaccurate result obtained. For these reason, the use of glass or plastic jars as sampling containers must be avoided.

Moisture content verification using the jar method of sampling cannot verify accuracy of 1 to 15 PPM$_w$.

SUMMARY OF THE INVENTION

It is therefore an object of the present invention to provide a method and apparatus for detecting moisture in a non-conductive fluid.

A further object of the present invention is to provide apparatus in the effluent of a filtration device to determine the amount of residual moisture concentration of a non-conductive fluid.

A still further object of the present invention is to provide a moisture detector capable of in-line sampling of a non-conductive fluid to determine the moisture concentration therein.

BRIEF DESCRIPTION OF THE DRAWINGS

The invention will be described in conjunction with the accompanying drawings, in which:

FIG. 1 is a schematic flow diagram of a system utilizing the present invention.

DETAILED DESCRIPTION OF PREFERRED EMBODIMENTS

Moisture detection in a non-conductive fluid is accomplished by the placement of a probe sensor 10 in the effluent of a filtration device to determine amount of residual moisture concentration. The stainless steel probe 10 encloses an aluminum oxide sensor which is a variable impedance device. It consists essentially of an oxidized silicon wafer base on top of which is a thin layer of aluminum with a porous surface of aluminum oxide. The aluminum oxide surface is overlaid with a thin film of gold. The gold and aluminum serve as electrodes. Water vapor diffuses through the porous gold film to the oxide surface. On absorbing water vapor the aluminum oxide changes its impedance. The quantity of moisture within the porous aluminum oxide structure affects the impedance of the capacitor formed. This impedance is measured by the electronic readout section of a monitor analyzer 12. The probe electronics convert the change of the capacitance into a moisture-proportional frequency signal. This more stable signal allows the use of ordinary connecting cable 14 between the probe and the electronic module up to 1000 feet, since the noise interference has no effect on this signal.

The analyzer electronics in monitor 12 receives the moisture and temperature frequency signals from the probe 10 and calculates the percent of saturation utilizing the after vapor pressure table and the probe calibration data programmed in an EPROM microprocessor. The analyzer provides six alarm set points for each, the high and the low alarm relay. The high alarm relay energizes when the measured value exceed the high set point and rising while the low alarm relay energizes when the measured value exceed the set point and decreasing.

Referring to FIG. 1, wherein there is shown schematically, the probe 10 is connected to monitor analyzer 12 by an ordinary connecting cable 14 such that the analyzer 12 may be positioned remote from the probe 10. Contaminated fluid such as non-conductive oil flows continuously in an operating system such as in and out of power plant reservoir, in and out of a filtration apparatus, and when necessary to be cleaned is routed by piping 16 to a filter 18 to remove large particles and the like and through conventional valving 20 to a detection chamber 22. An in-line flowmeter 24 controls the rate of flow through such system. A pressure transducer 26 may be utilized for monitoring the pressure in detection chamber 22. Fluid exiting the detection chamber is routed by way of piping 28 for further treatment or return to system as a result of the moisture condition detected by probe 10 and analyzed by monitor 12.

The sensor probe 10 monitors water vapor pressure and can calculate that value in any moisture unit such as dew point, PPM$_w$(parts per million by weight which is more common for liquid applications). System pressure is not a consideration since liquids, unlike gasses, are not compressible. Moisture in natural hydrocarbon or synthesized hydrocarbons may be accurately determined and with consistent repeatability of moisture levels down to 1 PPM by the application of the moisture monitor.

In order to obtain prompt, consistent and reliable data in the measurement of dissolved water, a moisture detector that provides in-line sampling is necessary. Sampling of moisture content by the monitor is obtained on line, while the fluid is in service or being transferred or processed. This closed system sampling method avoids contact with ambient air at the time of sampling, during transit and at the time of analysis.

The importance and need for this technology is very apparent in the Electric Power Industry. Oils, both natural or synthetic origin used in oil filled power transformers require total fluid moisture contents of less than 10 PPM. Verification of actual moisture content is not only assured with the monitor, an in-line device, but immediately displayed via LCD on the control panel for constant edification of operating personnel. And if desired, automatically direct fluid flow to a filtration device 30 for fluid reconditioning.

Incorporation of the monitor of the present invention on the effluent line of filtration devices, such as, mechanical filters, centrifuges, vacuum filters, provide, not only remote print-out or analog display of existing moisture content in $PPM_W$, but becomes a reasonable and economical processor control device; directing the fluid to recycle mode, return to service, or to clean a storage facility.

The monitor may be calibrated to function in moisture concentration environments of 1 to 15 $PPM_W$ to 500 to 1500 $PPM_W$. With this range, synthetic fluids, with their higher moisture concentration values compared to natural fluid, may also be successfully evaluated. Silicone liquid, for example, used for cooling and insulating and where a fire resistant material is required, has a moisture concentration of 900 $PPM_W$. Lubricating oils, such as turbine oil have a moisture concentration of 300 $PPM_W$ and hydraulic oils 550 $PPM_W$. All of the fluids may be successfully evaluated for moisture content with the moisture monitor.

The probe 10, of the present invention, is capable of determining:

(A) Actual water vapor pressure $PH2_o$; and
(B) Saturation vapor pressure of water at the temperature of the liquid $P_{sat}$.

Percent saturation = $PH2_o/P_{sat} \times 100$

The monitor analyzer 12 receives the above information from probe 10 and converts the information as follows:

$$PPM_W = PH2_o/100 \times C_S$$

or $$PPM_W = PH2_o/P_{sat} \times C_S$$

where $C_S$ = saturation concentration of water in a liquid at the temperature of measurement expressed in part per million by weight $PPM_W$. This value is obtained from published data of fluid supplier.

Although the present invention has been fully described in connection with the preferred embodiment thereof with reference to the accompanying drawings, it is to be noted that various changes and modifications are apparent to those skilled in the art. Such changes and modifications are to be understood as included within the scope of the present invention as defined by the appended claims, unless they depart therefrom.

What is claimed is:

1. A moisture monitor for in line determination of the amount of moisture in liquids, said moisture monitor comprising:
    a probe, said probe being immersed in and in contact with a continuous flow of a contaminated non-conductive liquid;
    a detection chamber, said detection chamber including means for determining vapor pressure of water at the temperature of said contaminated non-conductive liquid; and
    an analyzer monitor remote from said probe and in communication therewith; said analyzer monitor for manipulating information received from said probe to determine a moisture content of said contaminated non-conductive liquid.

2. The moisture monitor recited in claim 1, further comprising a filter provided in a liquid flow path prior to said detection chamber.

3. The moisture monitor recited in claim 2, further comprising means for treating said contaminated non-conductive liquid leaving said detection chamber in response to said moisture content.

4. The moisture monitor recited in claim 1, wherein said water vapor pressure is an actual vapor pressure.

5. The moisture monitor recited in claim 1, wherein said water vapor pressure is a saturation vapor pressure.

6. A method for determining the moisture content of a non-conductive liquid and method comprising the steps of:
    immersing a probe in direct contact with a flow of a non-conductive liquid;
    determining a water vapor pressure of said non-conductive liquid at the temperature of said non-conductive liquid based upon an impedance in said probe; and
    calculating a moisture content from said water vapor pressure.

7. The method recited in claim 6, wherein said water vapor pressure is an actual water vapor pressure and wherein said moisture content is determined by:

$$PPM_W = PH2_o/100 \times C_S$$

where $PPM_W$ = parts per million by weight, $C_S$ is a saturation concentration of water in a liquid at the liquid temperature and being expressed in parts per million by weight, and $PH2_o$ is said actual water vapor pressure.

8. The method recited in claim 6, where said water vapor pressure is a saturation vapor pressure and wherein said moisture content is determined by:

$$PPM_W = PH2_o/P_{sat} \times C_S$$

where $PPM_W$ = parts per million by weight, $C_S$ is a saturation concentration of water in a liquid at a liquid temperature and being expressed in parts per million by weight, $PH2_o$ is an actual water vapor pressure, and $P_{sat}$ is said saturation vapor pressure of water at the temperature of said liquid.

* * * * *